United States Patent [19]
Collette et al.

[11] Patent Number: 5,807,916
[45] Date of Patent: Sep. 15, 1998

[54] PROCESS FOR OBTAINING POLYMERS WHICH ARE SUPERABSORBENT FOR WATER AND AQUEOUS FLUIDS IN THE FORM OF PARTICLE AGGREGATES

[75] Inventors: Christian Collette; Manuel Hidalgo, both of Paris; André Kowalik, Gouvieux; Emmanuel Puchois, Paris; Shu-Rong Rebre, Vincennes, all of France

[73] Assignee: Elf Atochem S. A., Puteaux, France

[21] Appl. No.: 634,309

[22] Filed: Apr. 10, 1996

[30] Foreign Application Priority Data

Apr. 11, 1995 [FR] France ................... 95 04325

[51] Int. Cl.⁶ ............................................. C08F 6/22
[52] U.S. Cl. .................................................. 524/364
[58] Field of Search ............................... 524/364

[56] References Cited

U.S. PATENT DOCUMENTS 5,002,986  3/1991  Fujiura et al. ............ 525/371

*Primary Examiner*—Thomas R. Weber
*Attorney, Agent, or Firm*—Pennie & Edmonds LLP

[57] ABSTRACT

The process consists in the agglomeration of fine particles of superabsorbent polymer, carried out by introducing an aqueous solution of monomer into a slurry of aqueous polymer dispersed within a hydrocarbon liquid, this introduction being performed directly at the temperature and in conditions of polymerization of the monomer. A superabsorbent product is thus obtained in a very good yield, in the form of aggregates of particles such that the fraction passing through a 100-micron screen is less than 1%.

14 Claims, 1 Drawing Sheet

PROCESS FOR OBTAINING POLYMERS WHICH ARE SUPERABSORBENT FOR WATER AND AQUEOUS FLUIDS IN THE FORM OF PARTICLE AGGREGATES

The present specification relates to the production of polymer resins with high water absorptivity, in particular of absorbent resins in the form of agglomerated spherical particles.

BACKGROUND OF THE INVENTION

Such resins are particularly valued in the manufacture of sanitary products, including disposable nappies for babies, sanitary towels and similar products. They are also useful in other fields of application, for example in agriculture, as soil conditioners or as water-retaining agents, or else in civil engineering, as anti-condensation or dehydrating components in some materials of construction.

The choice of an appropriate absorbent resin involves taking into account a number of desirable properties like high absorbance, good compatibility with the other components of the sanitary products, low rewetting tendency, good mechanical strength of the water-swollen gel, which are properties that are rather connected with the chemical nature of the polymer, as well as particle sizes of between 100 and 1,000 micrometers, with a narrow distribution of these sizes and in particular with as few small-sized particles as possible, this being for reasons of handling and construction of the articles incorporating them, a high rate of absorption, and good diffusion of liquids into, between and within the absorbent particles, which are characteristics that are related to the particle size and the shape of the particles. In addition, a good water-absorbent resin must also be nonirritant and cheap.

The most widely known water-absorbing systems include partially neutralized polyacrylic acids and their derivatives, which the invention utilizes. Acrylic superabsorbent resins, which are among the essential subjects of the present invention, have traditionally been produced essentially by two different methods of polymerization: polymerization in solution, which yields polymer masses which must subsequently be ground again and classified to obtain a powder of particles of suitable particle size, and polymerization in inverse suspension, the direct result of which is a powder whose components are more or less spherical polymer particles.

This latter method of preparation, which is that with which the present invention is concerned, presents, however, the disadvantage of giving, in the absence of agglomeration, a superabsorbent polymer in the form of a powder of excessively fine particle size. This is the case, for example, with the processes for polymerization of an alkali metal salt of acrylic acid or of a closely related monomer in inverse water-in-oil suspension, as described in the Japanese Application No. 54-30710, which utilizes a primary surfactant consisting of an ester of a fatty acid and of sorbitan with an HLB of between 3 and 6, or Japanese Application No. 60-25045, which uses an anionic surfactant, which give powders whose particles are between 10 and 100 micrometers in size. Separate agglomeration of the initial individual particles is a known answer to the requirements of availability of final particles which are both of large size and which have the large specific surface without which the rate of water absorption would be insufficient. A number of agglomeration methods have been proposed. There is, for example, the agglomeration of dry powders, by surface crosslinking with a crosslinking agent (EP 349240, Nippon Shokubai) or by an aqueous solution of monomer containing a crosslinking agent (JP 1126314, Nippon Shokubai), which has the effect of improving the rate of absorption of the polymer, but is a technically tricky operation, which also has the disadvantage of giving relatively fragile agglomerates.

Others have therefore preferred the reagglomeration of a powder resuspended in an inert hydrocarbon liquid with the aid of an agglomerating agent consisting of an inorganic powder (silica) and of a surfactant (EP 224923 Seitetsu) or of a relatively small quantity of an acrylic aqueous solution introduced into the polymer suspension under polymerization conditions (WO 90/08789, Dow Chemicals).

These processes are merely methods for the recovery of powders which are unsatisfactory with regard to their particle size. It is, incidentally, an industrially somewhat unsatisfactory solution to have systematically to carry out two independent complete operations to give a single result. This is why others have incorporated the agglomeration stage into the overall process for the production of superabsorbent polymer by making the agglomeration stage follow directly the polymerization in inverse suspension, which gives the polymer in the form of individual particles. Thus, Mitsubishi (EP 522570) introduces monomer directly into the slurry from first polymerization, the polymerization of which is next brought about by heating the mixture to approximately 60° C. The method appears to function well, but in the case of small quantities of monomer. Sumitomo (EP 441507) also describes a two-stage preparation process in which, after having carried out the first stage of polymerization in inverse suspension, the suspension of polymer particles is cooled to ambient temperature so as to inactivate the surfactant which has ensured the stability of the inverse suspension; after which a second monomer charge, in the form of an aqueous solution, is added to the suspension, the polymerization of which is brought about by raising the temperature to about 60°/70° C. A narrow distribution of strongly bound large-sized agglomerates is thus obtained, but with the disadvantage of a high energy consumption and of poor output efficiency because of the slowness of the reactor cooling/heating cycles which are necessary.

SUMMARY OF THE INVENTION

The present invention overcomes these disadvantages by providing a process for obtaining superabsorbent polymer in the form of a powder of agglomerates of spherical particles by agglomeration of fine particles of superabsorbent polymer with the aid of an agglomerating agent consisting of an aqueous solution of monomer, in suspension in a medium which is a nonsolvent for the polymer and for the agglomerating agent, on condition that the following conditions are obeyed together:

the aqueous solution of monomer is introduced into the mixture at the temperature of polymerization of the monomer, the quantity of agglomerating monomer is between 50% and 200% by weight of the polymer to be agglomerated, the aqueous solution of monomer additionally contains a hydrophilic additive consisting of a thickener and of a surfactant with an HLB higher than or equal to 8.

Within the meaning of the present invention a temperature of polymerization is intended to mean a temperature at which the polymerization of the monomer is suitably carried out and which depends, among other things, on the polymerization initiator employed. In the case where this initiator is potassium persulphate, which is a preferred initiator for the invention, this temperature is higher than 50° C.

To carry out the invention, the starting point is either a fine powder of superabsorbent polymer which is dispersed while heated with moderate agitation in a hydrocarbon liquid medium, or directly the polymer slurry in the composition and temperature state which results from a preliminary polymerization in inverse suspension. The aqueous solution of unsaturated water-soluble monomer, which will have been prepared separately, is next introduced with agitation and while the temperature of the reactor is maintained as well as possible at the temperature of polymerization, in practice between 60° and 75° C. For this preparation, performed cold to prevent any untimely polymerization at this stage, the procedure is to dissolve and partially neutralize the monomer, to add polymerization initiator and, if appropriate, crosslinking agent, and an agglomerating agent intended to control the direct formation of clusters of polymer particles which will form the superabsorbent resin powder in its final form. The rate of introduction of the monomer solution and the agitation in the reactor are controlled so that the temperature within the reactor departs as little as possible from the chosen target temperature, since the addition of cold monomer tends to lower it, and the exothermicity of the polymerization to increase it. When the polymerization is finished, which is ensured when the temperature of the mixture has become steady again after passing through the exothermic peak, the water and the solvent are removed by distillation and the superabsorbent resin powder is collected directly in the form in which it is employed.

The unsaturated monomers, the polymerization initiators, the crosslinking agents, the nonreactive hydrocarbon liquids forming the dispersion medium, the surface-active agents and the thickeners which are involved in the invention are materials which are frequently encountered in radical polymerization processes in a disperse medium.

Acrylic acid and methacrylic acid are the preferred water-soluble unsaturated monomers of the invention. Nevertheless, the process may be carried out with other unsaturated water-soluble monomers like the methylpropanesulphonamides of these acids, their nonionic derivatives such as acrylamide, methacrylamide and their N,N-dimethylsubstituted derivatives, 2-hydroxyethyl acrylate or methacrylate, N-methylolacrylamide or -methacrylamide, or else their nitrogen-containing derivatives such as (dimethyl- or diethyl)amino(ethyl or propyl) acrylate or methacrylate and the corresponding quaternary ammonium salts.

The polymerization is initiated by radical polymerization initiators, water-soluble ones being preferred since both the monomer and the polymer are themselves hydrophilic; potassium persulphate is particularly suited in this case.

Crosslinking agents which can be employed for the partial crosslinking of the hydrophilic polymers produced generally consist of compounds containing at least two unsaturated groups capable of copolymerizing with the unsaturated monomer (acrylic acid), of the polyol di/triacrylate type, or which are capable of reacting with its polymerization products, like diol diglycidyl ethers.

The nonreactive hydrocarbon liquids employed as dispersion media for the invention are products that are chemically inert towards the monomers and the polymers formed. It is highly desirable that they should form an azeotrope with water, so that the latter may be removed by azeotropic distillation, and that their boiling point should be sufficiently low so that they may be evaporated from the final powder without thermal degradation. They are, for example, n-pentane, cyclohexane, n-heptane, toluene, ethylcyclohexane, isooctane and xylene.

It may happen that a spontaneous agglomeration of the polymer particles takes place in conditions that are close to those of the invention. It is obviously not possible to rely on such a process in order to obtain the industrial result which is sought after. This result is reached here by adding to the monomer agglomerating agent a highly hydrophilic agent with surfactant and viscosity-raising properties. This hydrophilic agent consists of the combination of a hydrophilic surfactant with an HLB higher than or equal to 8 and of a viscosity-raising or thickening agent. Hydrophilic surfactants which may be employed are, for example, nonionic agents like ethoxylated alkylphenols, sorbitan or ethoxylated sorbitol derivatives; among these, those containing 10 to 100 molecules, and more precisely 15 to 50 molecules, of ethylene oxide per molecule are particularly valued; or conventional ionic surfactants such as sulphates or sulphonates, for example sodium dodecylsulphate or dodecylbenzenesulphonic acid; or hydrophilic polymeric surface-active agents like polyvinyl alcohol or vinyl acetate/vinyl alcohol copolymers. The choice of the hydrophilic viscosity-raising agents or thickeners may turn to the cellulose derivatives known as modified water-soluble celluloses, such as carboxymethyl cellulose, or to water-soluble acrylic polymers like linear poly(meth)acrylic acids or their copolymers, for example with 2-hydroxyethyl acrylate, vinylpyrrolidone or its derivatives, linear (meth)acrylic acid/methyl vinyl ether/maleic acid or anhydride copolymers, their metal salts, polyethylene oxides and water-soluble polyurethanes. It will be noted that the use of a thickening or viscosity-raising agent in the charge of agglomerating agent is contrary to a prejudice of the prior art. What is desired from an agglomerating agent, whatever the mechanism by which it is consumed, is that it should bind onto or into the particles which it is intended to agglomerate and that it should not go into a stable suspension and polymerize in this form, the result of which would be the formation of a new population of individual polymer particles, which is obviously to be avoided. One of the unexpected teachings of the invention is that not only does a thickening agent in the charge of the agglomerating agent not promote its stabilization in the form of suspension, to the detriment of its contact with the polymer particles to be agglomerated, but that it is one of the characteristics of the process.

The weight ratio of the agglomerating agent to the polymer to be agglomerated is not without significance. Below 50% of agglomerating agent the agglomeration is only very partial and the final powder contains an excessively high proportion of fine beads which have remained independent. Above 200% the process suffers from difficulties in stabilization: there is too much disperse phase in the hydrocarbon which forms the dispersion medium, and there is a severe risk of setting solid.

EXAMPLES

Figure 1:
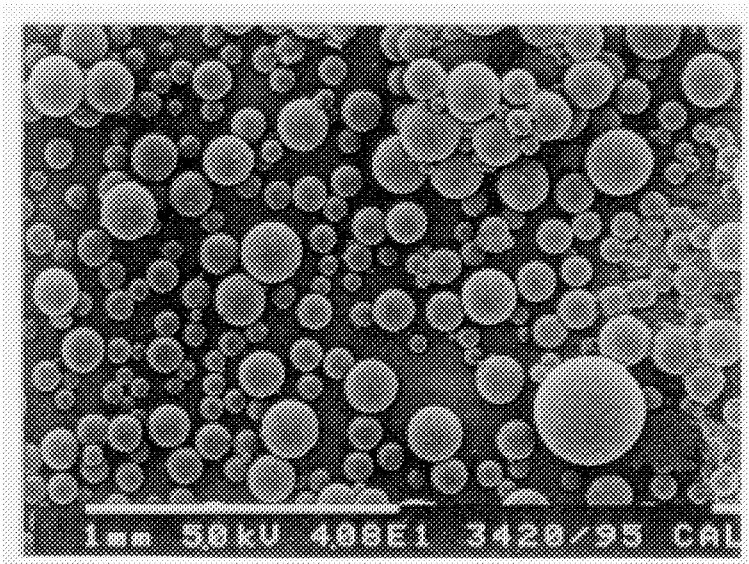
FIG. 1. Electron micrograph of superabsorbent polymer in the form of powder consisting of individual beads of superabsorbent polymer with a mean size of approximately 100 microns.
Figure 2:
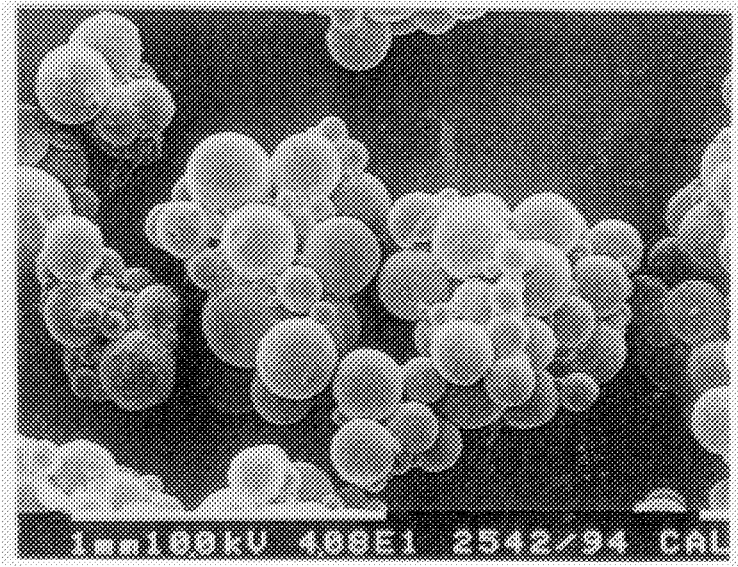
FIG. 2. Electron micrograph of superabsorbent polymer in the form of a powder of agglomerates of beads.

The examples which follow will improve the understanding of the invention.

Example 1
Preparation of superabsorbent particles without agglomeration (comparison example).

This is the one-step process based on polymerization in inverse suspension. The following are discerned therein:
- a sequence a of preparation of the dispersion medium,
- a sequence b of preparation of the monomer solution,
- a sequence c of introduction and dispersion of the monomer in the dispersion medium and its polymerization,
- a (final) sequence f of evaporation of the water and of the solvent and of recovery of the powder obtained.

Sequence a)

1.07 grams of a polyethylene modified with maleic anhydride (Hi-Wax 1105A, marketed under this name by Mitsui Petrochemical Industries Co) and 0.55 grams of sucrose di/tristearate are dissolved in 275 grams of heptane at about 80° C. and with stirring at 400 revolutions/minute and purging with nitrogen, in a one-liter reactor fitted with a device for introducing solid or liquid reactants, a bladed stirrer, a system for purging with inert gas, a temperature probe and a heating/cooling device consisting of a jacket in which a heat transfer fluid is circulated and can be assigned to a target temperature. This solution is kept at 80° C. for the time needed for the surfactant system to dissolve completely in the heptane. After dissolving, the temperature is brought back to 60° C.

Sequence b)

In another one-liter reactor equipped like the preceding one 92 grams of an aqueous solution containing 80% by weight of acrylic acid are neutralized with 135.59 grams of 22.62% sodium hydroxide lye, this being done slowly enough not to exceed 30° C. To this solution are added 2 grams of carboxymethyl cellulose and then 0.414 grams of a solution containing 2% by weight of ethylene glycol diglycidyl ether and 2.76 grams of an aqueous solution containing 2% of potassium persulphate.

Sequence c)

While the reactor with the heptane-based solution is kept stirred at 400 revolutions/minute and with nitrogen purging, the previously prepared aqueous phase is introduced rapidly into it and changes into an inverse suspension in the heptane. The rapid introduction of the aqueous phase into the reactor causes the temperature of the mixture to fall to about 40° C. This temperature is maintained for a stabilization period of 15 minutes. After this period the target temperature of the heat transfer fluid circulated in the jacket is raised to 70° C. The polymerization commences. The reactor is kept at this temperature level for 30 minutes.

Final sequence f)

The target temperature is now raised to 115°–130° C. to remove the water and heptane. After complete evaporation a superabsorbent polymer is obtained in the form of a powder consisting of individual beads (Figure I) of superabsorbent polymer with a mean size of approximately 100 microns, whose absorptivity for water containing salt in a concentration of 0.9% by weight is 75 grams per gram of polymer. The percentage of fines (particles smaller than 100 microns in size) is approximately 50%, a value which is quite unacceptable.

Examples 2 to 7 are examples of processes comprising a stage of agglomeration of individual fine particles. The following are discerned therein:
- sequences a, b and c, of preparation of the superabsorbent polymer as individual beads, which may be extemporaneous, and which are then linked directly into a series with the following sequences d, e and f, or else which correspond to a preliminary preparation of dry powder, in which case they have been followed by a sequence f of isolation of the powder,
- a sequence d of preparation of a charge of agglomerating agent,
- a sequence e of introduction of the agglomerating agent charged into the powder of individual beads of polymer or into a dispersing medium within which these beads remain in suspension, and optionally its polymerization if a polymerizable monomer agglomerating agent is involved,
- a second sequence f of evaporation of the solvents and of recovery of the powder obtained.

Example 2
Reagglomeration of powder according to the invention

Sequence a)

A reactor as described in the sequence a of the preceding examples is charged with 275 g of heptane. The temperature of the heat transfer fluid is set a target of the temperature of 80° C. and 1.07 grams of Hi-Wax 1105A and 0.55 grams of sucrose di/tristearate are dissolved therein with stirring at 400 revolutions/minute and with nitrogen purging. This solution is kept at 80° C. for the time needed for the dispersing system to dissolve in the heptane. The temperature is kept at 80° C. and the superabsorbent powder obtained in Example 1 is introduced into the mixture, stirring being continued, in such quantity that there are 92 g of dry polymer, allowing for the residual moisture in the powder.

Sequences b/c)

A quantity of water is introduced into the reactor such that, allowing for the moisture introduced by the superabsorbent, there are 138 g of water in the reactor (water content of the swollen superabsorbent polymer in suspension in the heptane medium equal to 60% by weight of the total polymer+water). The temperature of the heat transfer fluid is set a target of 70° C.

Sequence d)

While the preceding sequence is in progress, 92 grams of aqueous solution containing 80% by weight of acrylic acid are neutralized with 135.59 grams of 22.62% sodium hydroxide lye in a reactor equipped like that in sequence a, this being performed slowly enough not to exceed the temperature of 30° C. To this solution of partially neutralized acrylic acid (75 moles %) are added 2 grams of carboxymethyl cellulose and 0.46 grams of an aqueous solution containing 10% of nonylphenol ethoxylated with 50 moles of ethylene oxide (Remcopal 31250 from Ceca S.A.), and then 2.76 grams of an aqueous solution containing 2% by weight of potassium persulphate and 7 grams of an aqueous solution containing 2% of ethylene glycol diglycidyl ether.

Sequence e)

The monomer charge prepared in sequence d above is introduced dropwise into the reactor as it is at the end of sequence c. The introduction period is approximately 30 minutes, the temperature of the fluid in the jacket remaining set at 70° C., under nitrogen bubbling, the rate of stirring being maintained at 400–600 revolutions/minute. As a result of the introduction of this charge, which is relatively cold, the reactor temperature drops slightly without, however, ever falling below 65° C., and then rises again both because of the heating by the jacket at 70° C. and of the exothermicity of the polymerization reaction, which soon recommences. The rate of stirring is increased to 800 revolutions/minute and the reactor is kept in these conditions for about twenty minutes.

Final sequence f)

The target temperature is now raised to 115°–130° C. to remove the water and heptane. After complete evaporation a superabsorbent polymer is obtained in the form of a powder which appears under the microscope to be formed of agglomerates of polymer beads. The powder fraction passing through a 100-micron screen is smaller than 1%. The salt water absorption is 60 g/g of polymer.

Example 3

Two-stage process, polymerization and agglomeration according to the invention.

To begin with, stages a, b and c are performed as in Example 1.

The sequences d and e are next linked in series as in Example 2, and the operation is finished with a final sequence f, also as in Example 2.

A powder of superabsorbent polymer is thus obtained in the form of a powder of agglomerates of beads (Figure II), the undersize of which at 1 micrometer is lower than 1%, and whose salt water absorption is 62 g/g of polymer.

Example 4

Aqueous compositions according to the invention and temperature control according to Sumitomo The process is as in Example 3, except for the following differences.

The stage of polymerization of the monomer in inverse suspension resulting in the formation of a suspension of individual beads of monomer in the hydrocarbon solvent is carried out by performing the sequences a, b and c as in Example 1, but at the end of sequence c the target temperature of the reactor is set at 40° C. so as to bring the content of the reactor to this temperature. When this temperature is reached, the heating control of the jacket is switched off. The following sequence is then begun.

Sequence d)

While the preceding sequence is in progress, 92 grams of aqueous solution containing 80% by weight of acrylic acid are neutralized with 135.59 grams of 22.62% sodium hydroxide lye in a reactor equipped like that in sequence a, this being done slowly enough not to exceed the temperature of 30° C. To this solution of partially neutralized acrylic acid (75 moles %) are added 2 grams of carboxymethyl cellulose and 0.46 grams of an aqueous solution containing 10% of nonylphenol ethoxylated with 50 moles of ethylene oxide (Remcopal 31250 from Ceca S.A.), and then 2.76 grams of an aqueous solution containing 2% by weight of potassium persulphate and 2 grams of an aqueous solution containing 2% of ethylene glycol diglycidyl ether.

Sequence e)

The aqueous charge prepared according to sequence c is introduced dropwise into the reactor, with nitrogen bubbling, the rate of stirring being maintained at 400–600 revolutions/minute. The temperature of the content of the reactor decreases again to about 35° C. These conditions are maintained for approximately 15 minutes for stabilization and the heating control of the reactor is then brought back into action, the temperature of the heat transfer fluid being set a target of 70° C. The polymerization commences. These new conditions are maintained for about twenty minutes from the time when the temperature of the mixture has reached 70° C.

Final sequence f)

As in Example 1.

A powder which is substantially identical with that obtained in Example 3 is thus obtained, but at the expense of a greater experimental complexity, a longer production period and an appreciably higher consumption in the cooling/heating cycles in sequences c and f.

Example 5

Aqueous compositions according to Sumitomo, and temperature control according to the invention The procedure is as in Example 4, except for the following differences.

Sequence a)

275 g of heptane are introduced into the device described in Example 1 and are heated to 80° C., and 0.74 g of sucrose di/tristearate and 1.07 g of polyethylene modified with maleic anhydride are dissolved therein with stirring at 400 revolutions/minute.

Sequence b)

92 g of an aqueous solution containing 80% by weight of acrylic acid are separately neutralized with 135.59 g of 22% sodium hydroxide lye. 1 g of carboxymethyl cellulose is added, followed by 2.76 g of an aqueous solution containing 2% of potassium persulphate and 0.92 g of an aqueous solution containing 2% of ethylene glycol diglycidyl ether.

Sequence c)

While the reactor is kept stirred at 400 revolutions/minute and with nitrogen purging at the rate of 80 liters/minute, the aqueous phase prepared previously is introduced into it a little at a time and changes into inverse suspension in the heptane. The temperature is raised to 70° C. to induce polymerization; it is kept at this level for 30 minutes. The temperature is then brought back to 45° C.

Sequence d)

While the preceding operation is in progress, 92 g of aqueous solution containing 80% by weight of acrylic acid is separately neutralized with 135.59 g of 22.6% sodium hydroxide lye and then 2.76 g of an aqueous solution containing 2% of potassium persulphate and 0.92 g of an aqueous solution containing 2% of ethylene glycol diglycidyl ether are then added. This aqueous phase, which forms the monomer charge II is then brought back to 10° C.

Sequence e)

The stirring in the reactor is raised to 800 revolutions/minute, the nitrogen purging being maintained at 80 liters/minute. The charge d is introduced into it a little at a time. When the charge d has been introduced, the absorption is allowed to continue for 5 minutes at a temperature of 45° C. After this the temperature is raised to 70° C. to start the second stage of polymerization. The polymerization is allowed to continue for 30 minutes.

Final sequence f)

The heptane and most of the water are removed by distillation.

The final product is a powder whose mean particle size is 150 µm, whose undersize at 100 µm is unacceptable, with a value of more than 15%, and whose absorption of 0.9% salt water is 55 g/g.

Example 6

In this example the ability to conduct the operation at high temperature is exploited to the full. This is an advantageous alternative form of the preceding example.

Sequence a)

The procedure is as in Example 1, except for the difference that at the end of the sequence the temperature is brought back to 70° C. by setting the temperature of the heat transfer fluid in the reactor jacket at this temperature.

Sequence b)

An aqueous solution of monomer is prepared as in Example 1.

Sequence c)

While the reactor with the heptane-based solution is kept stirred at 400 revolutions/minute and with nitrogen purging, the previously prepared aqueous phase is introduced into it rapidly and changes into inverse suspension in the heptane.

The introduction of the aqueous phase into the reactor causes a brief drop in the temperature of the mixture, rapidly compensated by the fact that the jacket temperature is set a target of 70° C. The polymerization commences; its exothermicity can take the mixture to a higher temperature, brought back to 70° C. by the same mechanism as soon as the polymerization exothermicity ceases. A polymer suspension is formed and stays automatically at 70° C.

Sequence d)

While the preceding operation is in progress, a new charge of aqueous solution of monomer is prepared as described in sequence c of Example 3.

Sequences e) and f)

These are conducted like sequences e and f in Example 3.

A powder of superabsorbent polymer is thus obtained in the form of a powder of agglomerates of beads, whose undersize at 1 micrometer is less than 1%. Its salt water absorption is 65 g/g.

Example 7

Partial counter-examples

All the sequences take place as in the preceding example, with the exception of sequence d, in which the aqueous solution of monomer is prepared omitting the addition of the hydrophilic additive, that is to say of carboxymethyl cellulose and of nonylphenol ethoxylated with 50 moles of ethylene oxide.

A powder of superabsorbent polymer is thus obtained, consisting essentially of beads with an unacceptable 36% undersize at 100 microns.

If the nonylphenol ethoxylated with 50 moles of ethylene oxide is omitted, a powder containing 30% of fines is obtained. When it is the thickener that is omitted, the powder obtained contains 10% of fines.

The term "hlb" refers to hydrophilic-lipophilic balance, and its meaning and use are understood by one of ordinary skill in the surfactant art, as seen, for example, in U.S. Pat. Nos. 5,505,982, 5,503,755, and 5,474,776, which are incorporated by reference.

We claim:

1. A process for obtaining a superabsorbent polymer in the form of a powder of agglomerates of spherical particles by agglomeration of fine particles of a superabsorbent polymer by the steps of
    forming a mixture comprising fine particles of the superabsorbent polymer and a hydrocarbon liquid;
    combining with the mixture an aqueous solution of a monomer; and
    agglomerating the fine particles of the superabsorbent polymer in suspension in a hydrocarbon liquid medium which is a nonsolvent for the polymer and for the agglomerating agent, with the requirements that
        the aqueous solution of monomer is combined with the mixture at the temperature of polymerization of the monomer;
        the quantity of the monomer is between 50% and 200% by weight of the polymer; and
        the aqueous solution of the monomer contains a hydrophilic additive comprising
            a thickener and
            a surfactant with an HLB greater than or equal to 8.

2. The process according to claim 1, wherein the suspension of superabsorbent polymer to be agglomerated is produced by suspending a powder of superabsorbing polymer in a hydrocarbon liquid in which the polymer is not soluble.

3. The process according to claim 2, wherein before the agglomeration the superabsorbent polymer suspended in a hydrocarbon liquid in which it is not soluble is swollen with water.

4. The process according to claim 1, wherein the suspension of superabsorbent polymer to be agglomerated is a suspension as obtained by polymerization of an aqueous solution of monomer in inverse suspension in a hydrocarbon liquid in which the polymer and the agglomerating monomer are not soluble.

5. The process according to claim 1, wherein the aqueous solution of monomer for agglomeration is introduced into the mixture at a temperature of 60° C. to 75° C.

6. The process according to claim 1, wherein the thickener which is one of the components of the hydrophilic agent is selected from the group consisting of modified water-soluble celluloses, water-soluble acrylic polymers, and water-soluble acrylic copolymers.

7. The process according to claim 1, wherein the surfactant which is one of the components of the hydrophilic agent is selected from the group consisting of ethoxylated alkylphenols, ethoxylated sorbitan and ethoxylated sorbitol derivatives which contain 10 to 100 molecules of ethylene oxide per molecule.

8. The process according to claim 1, wherein the hydrophilic agent contains carboxymethyl cellulose as thickening agent and nonylphenol ethoxylated with 50 moles of ethylene oxide as hydroxylated surfactant.

9. A process for obtaining superabsorbent polymer in the form of a powder of agglomerates of spherical particles by agglomeration of fine particles of a superabsorbent polymer by
    combining a polymer to be agglomerated with a hydrocarbon liquid in a first container;
    forming an aqueous solution of an agglomerating monomer in a second container;
    stirring the contents of the first container; and
    introducing rapidly the contents of the second container into the first container, wherein
        the aqueous solution of the agglomerating monomer contacts the contents of the first container at the temperature of polymerization of the monomer;
        the quantity of agglomerating monomer is between 50% and 200% by weight of the polymer to be agglomerated; and
        the aqueous solution of the agglomerating monomer contains a hydrophilic additive comprising a thickener and a surfactant with an HLB greater than or equal to 8.

10. The process of claim 9 wherein the second container contains an initiator for polymerization of the monomer.

11. The process of claim 9 wherein the polymer to be agglomerated is polyethylene modified with maleic anhydride and sucrose distearate is combined with the organic liquid in the first container.

12. The process of claim 9 wherein the contents of the first container comprise an aqueous slurry of water, polymer to be agglomerated and organic liquid.

13. A process for obtaining superabsorbent polymer in the form of a powder of agglomerates of spherical particles by agglomeration of fine particles of a superabsorbent polymer by the steps of combining a polymer to be agglomerated with a hydrocarbon liquid to form a mixture;

forming an aqueous solution of an agglomerating monomer;

adding the aqueous solution of the agglomerating monomer to the mixture; and agglomerating the fine particles of the polymer, wherein the hydrocarbon liquid is a nonsolvent for the polymer and for the agglomerating monomer;

the aqueous solution of the agglomerating monomer is combined with the mixture at a temperature of polymerization of the monomer; and the quantity of monomer is between 50% and 200% by weight of the polymer.

14. The process of claim 13 wherein the agglomerating monomer comprises acrylic acid or a salt of acrylic acid.

* * * * *